US008389221B2

(12) United States Patent
Minekawa et al.

(10) Patent No.: US 8,389,221 B2
(45) Date of Patent: Mar. 5, 2013

(54) METHOD OF DETECTING H5 OR H7 AVIAN INFLUENZA VIRUS

(75) Inventors: Harumi Minekawa, Otawara (JP); Toshihiro Yonekawa, Otawara (JP); Takato Odagiri, Musashimurayama (JP)

(73) Assignees: Japan as represented by Director-General of National Institute of Infectious Diseases, Tokyo (JP); Eiken Kagaku Kabushiki Kaisha, Tokyo (JP)

(*) Notice: Subject to any disclaimer, the term of this patent is extended or adjusted under 35 U.S.C. 154(b) by 0 days.

(21) Appl. No.: 13/232,091

(22) Filed: Sep. 14, 2011

(65) Prior Publication Data

US 2012/0100527 A1    Apr. 26, 2012

Related U.S. Application Data

(62) Division of application No. 11/718,357, filed as application No. PCT/JP2005/019710 on Oct. 26, 2005, now Pat. No. 8,043,813.

(30) Foreign Application Priority Data

Nov. 1, 2004    (JP) .................................. 2004-318214
May 20, 2005   (JP) .................................. 2005-148487

(51) Int. Cl.
*C12Q 1/68*       (2006.01)
*C12P 19/34*     (2006.01)
*C07H 21/04*    (2006.01)

(52) U.S. Cl. .................... 435/6.12; 435/91.2; 536/24.33

(58) Field of Classification Search ........................ None
See application file for complete search history.

(56) References Cited

U.S. PATENT DOCUMENTS

| 7,504,109 B2 | 3/2009 | Yang et al. |
| 2004/0142319 A1 | 7/2004 | Yu et al. |

FOREIGN PATENT DOCUMENTS

| EP | 1 020 534 A1 | 7/2000 |
| EP | 1 310 565 A1 | 5/2003 |
| WO | WO 02/29118 A1 | 4/2002 |

OTHER PUBLICATIONS

Fouchier, R.A. et al. Avian influenza A virus (H7N7) associated with human conjuctivitis and a fatal case of acute respiratory distress syndrome. PNAS, vol. 101(5), p. 1356-1361, 2004.*
Lowe et al., A computer program for selection of oligonucleotide primers for polymerase chain reactions. Nucleic Acids Research, vol. 18, No. 7, pp. 1757-1761, 1990.*
Stratagene Catalog. gene characterization kits. Stratagene Catalog, p. 39, 1988.*

M. Munch, et al., "Detection and subtyping (H5 and H7) of avian type A influenza virus by reverse transcription-PCR and PCR-ELISA", Archives of Virology, vol. 146, No. 1, 2001, pp. 87-97.
Robert G. Webster, et al., "Characterization of H5N1 Influenza Viruses That Continue To Circulate in Geese in Southeastern China" Journal of Virology, vol. 76, No. 1, Jan. 2002. pp. 118-126.
Leo L. M. Poon, et al., "Detection of Human Influenza A Viruses by Loop-Mediated Isothermal Amplification", Journal of Clinical Microbiology, vol. 43, No. 1, Jan. 2005, pp. 427-430.
Lok-Ting Lau, et al., "Nucleic acid sequence-based amplification methods to detect avian influenza virus", Biochemical and Biophysical Research Communications, vol. 313, Jan. 9, 2004, pp. 336-342.
Songhua Shan, et al., "Comparison of nucleic acid-based detection of avian influenza H5N1 with virus isolation", Biochemical and Biphysical Research Communications, vol. 302, No. 2, Mar. 7, 2003, pp. 377-383.
Richard A. Collins, et al., "Rapid and sensitive detection of avian influenza virus subtype H7 using NASBA", Biochemical and Biophysical Research Communications, vol. 300, Jan. 10, 2003, pp. 507-515.
Ming-Shiuh Lee, et al., "Identification and subtyping of avian influenza viruses by reverse transcription-PCR", Journal of Virological Methods, vol. 97, Sep. 2001, 13-22.
Hong Thi Cam Thai, et al., "Development and Evaluation of a Novel Loop-Mediated Isothermal Amplification Method for Rapid Detection of Severe Acute Respiratory Syndrome Coronavirus", Journal of Clinical Microbiology, vol. 42, No. 5, XP-002981787, May 1, 2004, pp. 1956-1961.
Tetsushi Yoshikawa, et al., "Detection of Human Herpesvirus 7 DNA by Loop-Mediated Isothermal Amplification", Journal of Clinical Microbiology. vol. 42, No. 3, XP-002534230, Mar. 2004, pp. 1348-1352.
Manmohan Parida, et al., "Real-Time Reverse Transcription Loop-Mediated Isothermal Amplification for Rapid Detection of West Nile Virus", Journal of Clinical Microbiology, vol. 42. No. 1, XP-002534231, Jan. 2004, pp. 257-263.
Tsugunori Notomi, et al., "Loop-mediated isothermal amplification of DNA", Oxford University Press, vol. 28, No. 12, XP007905272, Dec. 1, 2000, 7 pages.
Masaki Imai, et al., "Development of H5-RT-LAMP (loop-mediated isothermal amplification) system for rapid diagnosis of H5 avian Influenza virus Infection", Vaccine, Elsevier, vol. 24, No. 44-46, XP025152002, Nov. 10, 2006, pp. 6679-6682.
Ron A. M. Fouchier, et al., "Avian Influenza A Virus (H7N7) Associated with Human Conjunctivitis and a Fatal Case of Acute Respiratory Distress Syndrome", PNAS (Proc. Natl. Acad. Sol.), vol. 101, No. 5, Feb. 3, 2004, pp. 1356-1361.

* cited by examiner

*Primary Examiner* — Suryaprabha Chunduru
(74) *Attorney, Agent, or Firm* — Oblon, Spivak, McClelland, Maier & Neustadt, L.L.P.

(57) ABSTRACT

The present invention provides oligonucleotide primers specifically hybridizing to an arbitrary nucleotide sequence designed from the nucleotide sequence of hemagglutinin of an H5 or H7 avian influenza virus, a nucleic acid amplification method using the primers, a method for diagnosis of infection with an H5 or H7 avian influenza virus by detection of nucleic acid amplification, and a kit for influenza diagnosis.

5 Claims, 9 Drawing Sheets

(a)

(b)

(a)

(b)

(a)

(b)

METHOD OF DETECTING H5 OR H7 AVIAN INFLUENZA VIRUS

CROSS-REFERENCE TO RELATED APPLICATIONS

The present application is a divisional of U.S. patent application Ser. No. 11/718,357, filed on Aug. 23, 2007 now U.S. Pat. No. 8,043,813, which is a 35 U.S.C. §371 National Stage patent application of International patent application PCT/JP2005/019710, filed on Oct. 26, 2005, which claims priority to Japanese patent applications JP 2005-148487, filed on May 20, 2005, and JP 2004-318214, filed on Nov. 1, 2004.

TECHNICAL FIELD

The present invention relates to a method for detection of an H5 or H7 avian influenza virus. More particularly, the present invention relates to oligonucleotide primers for detection of an H5 or H7 avian influenza virus, a method for detection of an H5 or H7 avian influenza virus using the primers, a method for influenza diagnosis, and a kit for influenza diagnosis.

BACKGROUND ART

Influenza, which is an epidemic viral respiratory infection, affects people of the wide age bracket from infants to the old aged and is often fatal. Currently controversial H5 avian influenza viruses that infect birds do not originally infect humans. However, human infection with the viruses was confirmed in Hong Kong in 1997 and was prevalent with the result that 6 of 18 patients died. Fortunately, no human infection had been confirmed thereafter. However, human infection was confirmed in Thailand and Vietnam in 2004 with the result that 8 and 16 persons died in Thailand and Vietnam, respectively.

Highly pathogenic avian influenza viruses include an H7 subtype, in addition to the H5 subtype. The H7 subtypes are broadly divided into Eurasian and American subtypes according to the sequences thereof. According to reports, the H7 avian influenza viruses killed 1 person when prevalent in Netherlands in 2003, and were also prevalent in USA from 2003 through 2004.

A kit for quick diagnosis of a human influenza virus A has been used currently in the detection of avian influenza viruses. However, the identification of a virus subtype that causes infection has required further detailed analysis such as the antigenic analysis or genetic test of separated viruses.

Diagnosis using virus separation and culture that produces accurate results requires several days and therefore, cannot be conducted quickly. There are several methods capable of quick diagnosis as compared with the virus separation. Among them, an RT-PCR method has been said to have high detection sensitivity as compared with other methods. However, according to some reports, currently disclosed RT-PCR methods cannot detect the viruses with high sensitivity as compared with viral infectivity. Thus, infection with an avian influenza virus cannot be denied even if a result is negative in a test using the RT-PCR method.

Thus, a test method capable of quickly detecting an H5 or H7 avian influenza virus with high sensitivity has been demanded.

Patent Document 1: European Patent Publication No. 1310565
Patent Document 2: Japanese Published PCT Translation No. 2004
Non-Patent Document 1: Lau L T., et al., Biochem. Biophys. Res. Commun., vol. 313, p. 336-342 (2004)
Non-Patent Document 2: Shan S., et al., Biochem. Biophys. Res. Commun., vol. 302, p. 377-383 (2003)
Non-Patent Document 3: Collins R A., et al., Biochem. Biophys. Res. Commun., vol. 300, p. 507-515 (2003)
Non-Patent Document 4: Lee M S., et al., J. Virol. Methods, vol. 97, p. 13-22 (2001)
Non-Patent Document 5: Munch M., et al., Arch. Virol., vol. 146, p. 87-97 (2001)

DISCLOSURE OF THE INVENTION

Problems to be Solved by the Invention

The present inventors have conducted diligent studies for solving the problems and have consequently completed the present invention by finding out that an H5 or H7 avian influenza virus can be detected with high sensitivity by preparing oligonucleotide primers hybridizing to a nucleotide sequence specific to the H5 or H7 avian influenza virus and amplifying the nucleotide sequence specific to the H5 or H7 avian influenza virus by a LAMP (loop-mediated isothermal amplification) method.

Means for Solving the Problems

Specifically, the present invention provides the following (1) to (8):
(1) Oligonucleotide primers designed from arbitrary nucleotide sequences or complementary nucleotide sequences thereof, selected from a nucleotide sequence at the 693rd to 959th positions in the hemagglutinin nucleotide sequence of an H5 avian influenza virus represented by SEQ ID NO: 1.
(2) The oligonucleotide primers according to (1), comprising an oligonucleotide selected from the following (a) to (c):
(a) an oligonucleotide comprising at least consecutive 15 bases selected from the nucleotide sequences represented by SEQ ID NOs: 2 to 7 or complementary nucleotide sequences thereof;
(b) an oligonucleotide capable of hybridizing under stringent conditions to the oligonucleotide (a); and
(c) an oligonucleotide comprising a nucleotide sequence of the oligonucleotide (a) or (b) with the substitution, deletion, insertion, or addition of one or several bases and having a primer function.
(3) The oligonucleotide primers according to (1) or (2), characterized by comprising a nucleotide sequence selected from the following (a) to
(d), when F3c, F2c, and F1c nucleotide sequence regions and B3, B2, and B1 nucleotide sequence regions are selected from the 3' end side and from the 5' end side, respectively, of a target nucleic acid of hemagglutinin of the H5 avian influenza virus and their respective complementary nucleotide sequences are defined as F3, F2, and F1 and as B3c, B2c, and B1c:
(a) a nucleotide sequence having the F2 region of the target nucleic acid at the 3' end side and having the F1c region of the target nucleic acid at the 5' end side;
(b) a nucleotide sequence having the F3 region of the target nucleic acid;
(c) a nucleotide sequence having the B2 region of the target nucleic acid at the 3' end side and having the B1c region of the target nucleic acid at the 5' end side; and
(d) a nucleotide sequence having the B3 region of the target nucleic acid.

(4) The oligonucleotide primers according to any one of (1) to (3), characterized by being capable of amplifying a nucleotide sequence specific to the H5 avian influenza virus and comprising a nucleotide sequence selected from the following (a) to (b) in the 5' end to 3' end direction:
(a) 5'-(a nucleotide sequence complementary to the nucleotide sequence of SEQ ID NO: 2)-(an arbitrary nucleotide sequence having 0 to 50 bases)-(the nucleotide sequence of SEQ ID NO: 3)-3'; and
(b) 5'-(the nucleotide sequence of SEQ ID NO: 5)-(an arbitrary nucleotide sequence having 0 to 50 bases)-(a nucleotide sequence complementary to the nucleotide sequence of SEQ ID NO: 6)-3'.
(5) A method for detection of an H5 avian influenza virus, characterized by comprising performing an amplification reaction of a target nucleic acid region of an H5 avian influenza virus by use of oligonucleotide primers according to any one of (1) to (4).
(6) The method for detection of an H5 avian influenza virus according to (5), characterized in that the amplification reaction of a target nucleic acid region of an H5 avian influenza virus is a LAMP method.
(7) A method for influenza diagnosis, characterized by comprising detecting amplification of a target nucleic acid region of an H5 avian influenza virus by use of oligonucleotide primers according to any one of (1) to (4) and thereby diagnosing the presence or absence of infection with the H5 avian influenza virus.
(8) A kit for influenza diagnosis, characterized by comprising oligonucleotide primers according to any one of (1) to (4).

The present invention also provides the following (9) to (16):
(9) Oligonucleotide primers designed from arbitrary nucleotide sequences or complementary nucleotide sequences thereof, selected from a nucleotide sequence at the 19th to 220th positions in the hemagglutinin nucleotide sequence of an H5 avian influenza virus represented by SEQ ID NO: 1.
(10) The oligonucleotide primers according to (9), comprising an oligonucleotide selected from the following (a) to (c):
(a) an oligonucleotide comprising at least consecutive 15 bases selected from the nucleotide sequences represented by SEQ ID NOs: 13 to 18 or complementary nucleotide sequences thereof;
(b) an oligonucleotide capable of hybridizing under stringent conditions to the oligonucleotide (a); and
(c) an oligonucleotide comprising a nucleotide sequence of the oligonucleotide (a) or (b) with the substitution, deletion, insertion, or addition of one or several bases and having a primer function.
(11) The oligonucleotide primers according to (9) or (10), characterized by comprising a nucleotide sequence selected from the following (a) to (d), when F3c, F2c, and F1c nucleotide sequence regions and B3, B2, and B1 nucleotide sequence regions are selected from the 3' end side and from the 5' end side, respectively, of a target nucleic acid of hemagglutinin of the H5 avian influenza virus and their respective complementary nucleotide sequences are defined as F3, F2, and F1 and as B3c, B2c, and B1c:
(a) a nucleotide sequence having the F2 region of the target nucleic acid at the 3' end side and having the F1c region of the target nucleic acid at the 5' end side;
(b) a nucleotide sequence having the F3 region of the target nucleic acid;
(c) a nucleotide sequence having the B2 region of the target nucleic acid at the 3' end side and having the B1c region of the target nucleic acid at the 5' end side; and
(d) a nucleotide sequence having the B3 region of the target nucleic acid.
(12) The oligonucleotide primers according to any one of (9) to (11), characterized by being capable of amplifying a nucleotide sequence specific to the H5 avian influenza virus and comprising a nucleotide sequence selected from the following (a) to (b) in the 5' end to 3' end direction:
(a) 5'-(a nucleotide sequence complementary to the nucleotide sequence of SEQ ID NO: 13)-(an arbitrary nucleotide sequence having 0 to 50 bases)-(the nucleotide sequence of SEQ ID NO: 14)-3'; and
(b) 5'-(the nucleotide sequence of SEQ ID NO: 16)-(an arbitrary nucleotide sequence having 0 to 50 bases)-(a nucleotide sequence complementary to the nucleotide sequence of SEQ ID NO: 17)-3'.
(13) A method for detection of an H5 avian influenza virus, characterized by comprising performing an amplification reaction of a target nucleic acid region of an H5 avian influenza virus by use of oligonucleotide primers according to any one of (9) to (12).
(14) The method for detection of an H5 avian influenza virus according to (13), characterized in that the amplification reaction of a target nucleic acid region of an H5 avian influenza virus is a LAMP method.
(15) A method for influenza diagnosis, characterized by comprising detecting amplification of a target nucleic acid region of an H5 avian influenza virus by use of oligonucleotide primers according to any one of (9) to (12) and thereby diagnosing the presence or absence of infection with the H5 avian influenza virus.
(16) A kit for influenza diagnosis, characterized by comprising oligonucleotide primers according to any one of (9) to (12).

The present invention also provides the following (17) to (24):
(17) Oligonucleotide primers designed from arbitrary nucleotide sequences or complementary nucleotide sequences thereof, selected from a nucleotide sequence at the 114th to 333rd positions in the hemagglutinin nucleotide sequence of an H5 avian influenza virus represented by SEQ ID NO: 1.
(18) The oligonucleotide primers according to (17), characterized by comprising an oligonucleotide selected from the following (a) to (c):
(a) an oligonucleotide comprising at least consecutive 15 bases selected from the nucleotide sequences represented by SEQ ID NOs: 24 to 29 or complementary nucleotide sequences thereof;
(b) an oligonucleotide capable of hybridizing under stringent conditions to the oligonucleotide (a); and
(c) an oligonucleotide comprising a nucleotide sequence of the oligonucleotide (a) or (b) with the substitution, deletion, insertion, or addition of one or several bases and having a primer function.
(19) The oligonucleotide primers according to (17) or (18), characterized by comprising a nucleotide sequence selected from the following (a) to (d), when F3c, F2c, and F1c nucleotide sequence regions and B3, B2, and B1 nucleotide sequence regions are selected from the 3' end side and from the 5' end side, respectively, of a target nucleic acid of hemagglutinin of the H5 avian influenza virus and their respective complementary nucleotide sequences are defined as F3, F2, and F1 and as B3c, B2c, and B1c:
(a) a nucleotide sequence having the F2 region of the target nucleic acid at the 3' end side and having the F1c region of the target nucleic acid at the 5' end side;
(b) a nucleotide sequence having the F3 region of the target nucleic acid;

(c) a nucleotide sequence having the B2 region of the target nucleic acid at the 3' end side and having the B1c region of the target nucleic acid at the 5' end side; and (d) a nucleotide sequence having the B3 region of the target nucleic acid.

(20) The oligonucleotide primers according to any one of (17) to (19), characterized by being capable of amplifying a nucleotide sequence specific to the H5 avian influenza virus and comprising a nucleotide sequence selected from the following (a) to (b) in the 5' end to 3' end direction:

(a) 5'-(a nucleotide sequence complementary to the nucleotide sequence of SEQ ID NO: 24)-(an arbitrary nucleotide sequence having 0 to 50 bases)-(the nucleotide sequence of SEQ ID NO: 25)-3'; and (b) 5'-(the nucleotide sequence of SEQ ID NO: 27)-(an arbitrary nucleotide sequence having 0 to 50 bases)-(a nucleotide sequence complementary to the nucleotide sequence of SEQ ID NO: 28)-3'.

(21) A method for detection of an H5 avian influenza virus, characterized by comprising performing an amplification reaction of a target nucleic acid region of an H5 avian influenza virus by use of oligonucleotide primers according to any one of (17) to (20).

(22) The method for detection of an H5 avian influenza virus according to (21), characterized in that the amplification reaction of a target nucleic acid region of an H5 avian influenza virus is a LAMP method.

(23) A method for influenza diagnosis, characterized by comprising detecting amplification of a target nucleic acid region of an H5 avian influenza virus by use of oligonucleotide primers according to any one of (17) to (20) and thereby diagnosing the presence or absence of infection with the H5 avian influenza virus.

(24) A kit for influenza diagnosis, characterized by comprising oligonucleotide primers according to any one of (17) to (20).

The present invention also provides the following (25) to (32):

(25) Oligonucleotide primers designed from arbitrary nucleotide sequences or complementary nucleotide sequences thereof, selected from a nucleotide sequence at the 874th to 1065th positions in the hemagglutinin nucleotide sequence of an H5 avian influenza virus represented by SEQ ID NO: 1.

(26) The oligonucleotide primers according to (25), characterized by comprising an oligonucleotide selected from the following (a) to (c):

(a) an oligonucleotide comprising at least consecutive 15 bases selected from the nucleotide sequences represented by SEQ ID NOs: 35 to 40 or complementary nucleotide sequences thereof;

(b) an oligonucleotide capable of hybridizing under stringent conditions to the oligonucleotide (a); and (c) an oligonucleotide comprising a nucleotide sequence of the oligonucleotide (a) or (b) with the substitution, deletion, insertion, or addition of one or several bases and having a primer function.

(27) The oligonucleotide primers according to (25) or (26), characterized by comprising a nucleotide sequence selected from the following (a) to (d), when F3c, F2c, and F1c nucleotide sequence regions and B3, B2, and B1 nucleotide sequence regions are selected from the 3' end side and from the 5' end side, respectively, of a target nucleic acid of hemagglutinin of the H5 avian influenza virus and their respective complementary nucleotide sequences are defined as F3, F2, and F1 and as B3c, B2c, and B1c:

(a) a nucleotide sequence having the F2 region of the target nucleic acid at the 3' end side and having the F1c region of the target nucleic acid at the 5' end side;

(b) a nucleotide sequence having the F3 region of the target nucleic acid;

(c) a nucleotide sequence having the B2 region of the target nucleic acid at the 3' end side and having the B1c region of the target nucleic acid at the 5' end side; and (d) a nucleotide sequence having the B3 region of the target nucleic acid.

(28) The oligonucleotide primers according to any one of (25) to (27), characterized by being capable of amplifying a nucleotide sequence specific to the H5 avian influenza virus and comprising a nucleotide sequence selected from the following (a) to (b) in the 5' end to 3' end direction:

(a) 5'-(a nucleotide sequence complementary to the nucleotide sequence of SEQ ID NO: 35)-(an arbitrary nucleotide sequence having 0 to 50 bases)-(the nucleotide sequence of SEQ ID NO: 36)-3'; and (b) 5'-(the nucleotide sequence of SEQ ID NO: 38)-(an arbitrary nucleotide sequence having 0 to 50 bases)-(a nucleotide sequence complementary to the nucleotide sequence of SEQ ID NO: 39)-3'.

(29) A method for detection of an H5 avian influenza virus, characterized by comprising performing an amplification reaction of a target nucleic acid region of an H5 avian influenza virus by use of oligonucleotide primers according to any one of (25) to (28).

(30) The method for detection of an H5 avian influenza virus according to (29), characterized in that the amplification reaction of a target nucleic acid region of an H5 avian influenza virus is a LAMP method.

(31) A method for influenza diagnosis, characterized by comprising detecting amplification of a target nucleic acid region of an H5 avian influenza virus by use of oligonucleotide primers according to any one of (25) to (28) and thereby diagnosing the presence or absence of infection with the H5 avian influenza virus.

(32) A kit for influenza diagnosis, characterized by comprising oligonucleotide primers according to any one of (25) to (28).

The present invention further provides the following (33) to (40):

(33) Oligonucleotide primers designed from arbitrary nucleotide sequences or complementary nucleotide sequences thereof, selected from a nucleotide sequence at the 1016th to 1225th positions in the hemagglutinin nucleotide sequence of an H7 avian influenza virus represented by SEQ ID NO: 48.

(34) The oligonucleotide primers according to (33), characterized by comprising an oligonucleotide selected from the following (a) to (c):

(a) an oligonucleotide comprising at least consecutive 15 bases selected from the nucleotide sequences represented by SEQ ID NOs: 49 to 54 or complementary nucleotide sequences thereof;

(b) an oligonucleotide capable of hybridizing under stringent conditions to the oligonucleotide (a); and (c) an oligonucleotide comprising a nucleotide sequence of the oligonucleotide (a) or (b) with the substitution, deletion, insertion, or addition of one or several bases and having a primer function.

(35) The oligonucleotide primers according to (33) or (34), characterized by comprising a nucleotide sequence selected from the following (a) to (d), when F3c, F2c, and F1c nucleotide sequence regions and B3, B2, and B1 nucleotide sequence regions are selected from the 3' end side and from the 5' end side, respectively, of a target nucleic acid of hemagglutinin of the H7 avian influenza virus and their respective complementary nucleotide sequences are defined as F3, F2, and F1 and as B3c, B2c, and B1c:

(a) a nucleotide sequence having the F2 region of the target nucleic acid at the 3' end side and having the F1c region of the target nucleic acid at the 5' end side;
(b) a nucleotide sequence having the F3 region of the target nucleic acid;
(c) a nucleotide sequence having the B2 region of the target nucleic acid at the 3' end side and having the B1c region of the target nucleic acid at the 5' end side; and
(d) a nucleotide sequence having the B3 region of the target nucleic acid.

(36) The oligonucleotide primers according to any one of (33) to (35), characterized by being capable of amplifying a nucleotide sequence specific to the H7 avian influenza virus and comprising a nucleotide sequence selected from the following (a) to (b) in the 5' end to 3' end direction:

(a) 5'-(a nucleotide sequence complementary to the nucleotide sequence of SEQ ID NO: 49)-(an arbitrary nucleotide sequence having 0 to 50 bases)-(the nucleotide sequence of SEQ ID NO: 50)-3'; and
(b) 5'-(the nucleotide sequence of SEQ ID NO: 52)-(an arbitrary nucleotide sequence having 0 to 50 bases)-(a nucleotide sequence complementary to the nucleotide sequence of SEQ ID NO: 53)-3'.

(37) A method for detection of an H7 avian influenza virus, characterized by comprising performing an amplification reaction of a target nucleic acid region of an H7 avian influenza virus by use of oligonucleotide primers according to any one of (33) to (36).

(38) The method for detection of an H7 avian influenza virus according to (37), characterized in that the amplification reaction of a target nucleic acid region of an H7 avian influenza virus is a LAMP method.

(39) A method for influenza diagnosis, characterized by comprising detecting amplification of a target nucleic acid region of an H7 avian influenza virus by use of oligonucleotide primers according to any one of (33) to (36) and thereby diagnosing the presence or absence of infection with the H7 avian influenza virus.

(40) A kit for influenza diagnosis, characterized by comprising oligonucleotide primers according to any one of (33) to (36).

Effect of the Invention

According to the present invention, an H5 or H7 avian influenza virus can be detected quickly with high sensitivity by preparing oligonucleotide primers selectively hybridizing to a nucleotide sequence specific to the H5 or H7 avian influenza virus and amplifying the nucleotide sequence specific to the H5 or H7 avian influenza virus by a LAMP method.

BRIEF DESCRIPTION OF THE DRAWINGS

FIGS. 1(a), 1(b), 1(c), and 1(d) show results obtained using primer sets A, B, C, and D, respectively. NC represents a negative control, H1 represents New Caledonia, H3 represents Panama, and PC represents a positive control (H5 subtype plasmid DNA);

FIGS. 2(a), 2(b), 2(c), and 2(d) show results obtained using the primer sets A, B, C, and D, respectively. $10^3$ to $10^6$ represent dilution rates of RNA extracts;

FIG. 4 is a graph showing a result of a cross matching test of the primer set for an H5 avian influenza virus. B-sd represents B/Shandong/07/97, B-sh represents B/Shanghai/361/2002, and AIV-H1 and so on represents an avian influenza virus H1 and so on;

FIG. 8(a) represents A/Netherlands/219/2003, and FIG. 8(b) represents A/Netherlands/33/2003. $10^5$ to $10^8$ represent dilution rates of RNA extracts; FIG. 9(a) represents A/mallard/Netherlands/12/00, and FIG. 9(b) represents A/wigeon/Osaka/1/2001. $10^5$ to $10^8$ represent dilution rates of RNA extracts.

BEST MODE FOR CARRYING OUT THE INVENTION

Figure 1:
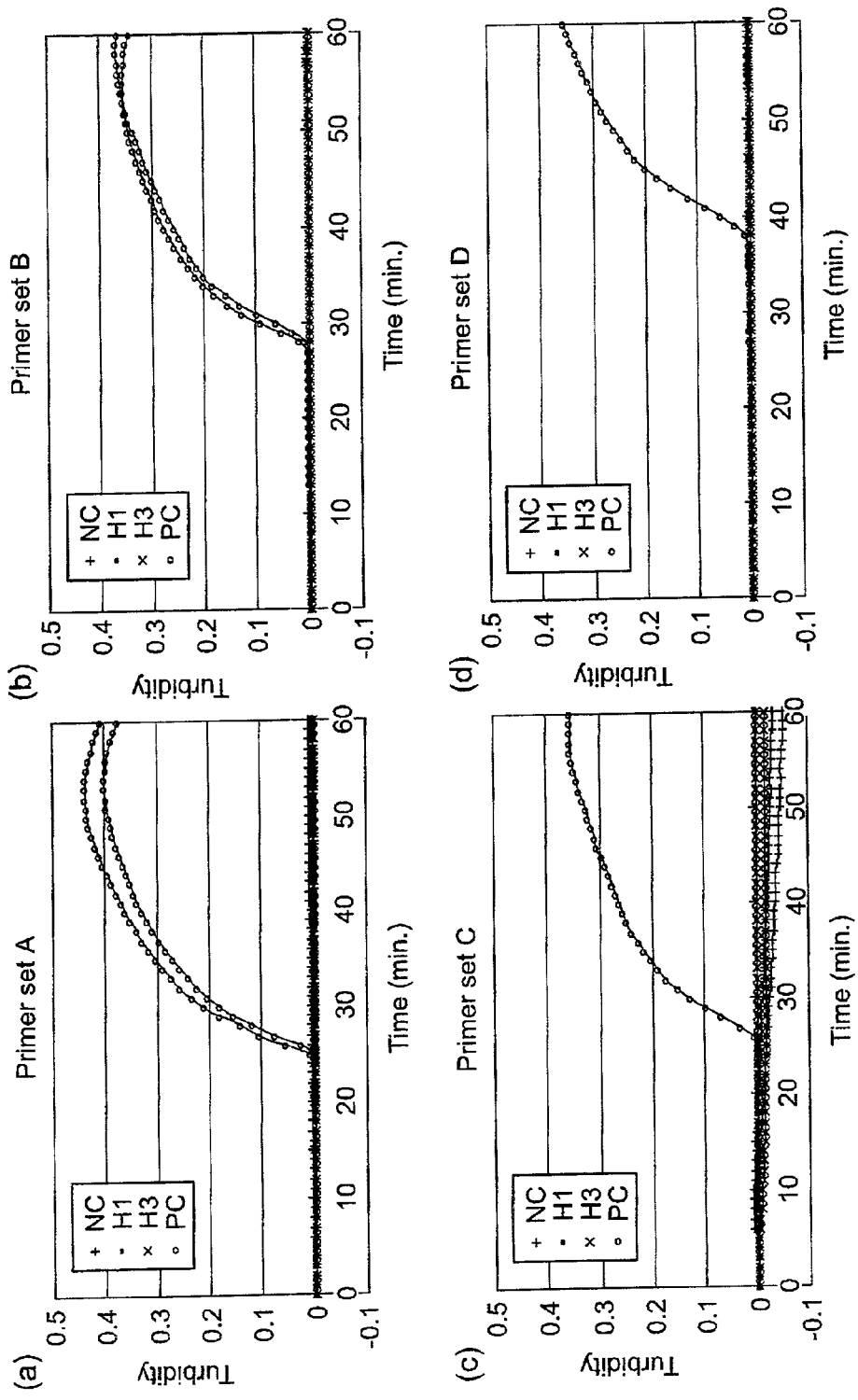
FIG. 1 is a graph showing a result of a specificity test of primer sets for an H5 avian influenza virus.

A sample used in the present invention includes samples derived from human or other animal living bodies suspected of being infected with an influenza virus, for example, sputum, bronchoalveolar lavage fluids, nasal secretions, nasal aspirates, nasal lavage fluids, nasal swabs, pharyngeal swabs, throat washings, saliva, blood, serums, plasmas, spinal fluids, urine, feces, and tissues. Alternatively, cells or culture solutions thereof used in infection experiments or the like, or virus-containing samples separated from living body-derived samples or cultured cells may also be used as the sample. These samples may be subjected to pretreatment such as separation, extraction, condensation, and purification.

Such nucleic acid amplification is achieved by a loop-mediated isothermal amplification method called a LAMP method developed by Notomi et al., which is a novel nucleic acid amplification method that does not require temperature control allegedly indispensable for PCR methods (Pamphlet of International Publication No. WO 00/28082). This method is a nucleic acid amplification method that allows for a complementary strand synthesis reaction under isothermal conditions by allowing a nucleotide serving as a template to anneal with its own 3' end and initiating complementary strand synthesis from this origin while combining primers annealing to this formed loop. Moreover, the LAMP method is a highly specific nucleic acid amplification method using 4 primers that recognize at least 6 regions.

Oligonucleotide primers used in the LAMP method are at least 4 primers that recognize the nucleotide sequences of 6 regions in total, that is, F3c, F2c, and F1c regions from the 3' end side and B3, B2, and B1 regions from the 5' end side, of the nucleotide sequence of a template nucleic acid, and are respectively called inner primers F and B and outer primers F and B. Complementary sequences of F1c, F2c, and F3c are called F1, F2, and F3, respectively. Complementary sequences of B1, B2, and B3 are called B1c, B2c, and B3c, respectively. The inner primer is an oligonucleotide having, at the 3' end, a nucleotide sequence that recognizes a "certain nucleotide sequence region" in a target nucleotide sequence and provides a synthesis origin and having, at the 5' end, a nucleotide sequence complementary to an arbitrary region of a nucleic acid synthesis reaction product obtained with this primer at the origin. In this context, a primer comprising a "nucleotide sequence selected from F2" and a "nucleotide sequence selected from F1c" is called an inner primer F (hereinafter, abbreviated to FIP), and a primer comprising a "nucleotide sequence selected from B2" and a "nucleotide sequence selected from B1c" is called an inner primer B (hereinafter, abbreviated to BIP). On the other hand, the outer primer is an oligonucleotide having a nucleotide sequence that recognizes a "certain nucleotide sequence region present nearer to the 3' end side than the regions recognized by the inner primers" in the target nucleotide sequence and provides a synthesis origin. In this context, a primer comprising a "nucleotide sequence selected from F3" is called an outer primer F (hereinafter, abbreviated to F3), and a primer comprising a "nucleotide sequence selected from B3" is called an outer primer B (hereinafter, abbreviated to B3). In this context, F in each primer indicates that the primer complementarily binds to the sense strand of the target nucleotide sequence and provides a synthesis origin. On the other hand, B in each primer indicates that the primer complementarily binds to the antisense strand of the target nucleotide sequence and provides a synthesis origin. In this context, the oligonucleotide used as the primer is 10 bases or more, preferably 15 bases or more, in length, and may be either synthesized chemically or natural. Each primer may be a single oligonucleotide or a mixture of several oligonucleotides.

In the LAMP method, additional primers, that is, loop primers, can further be used in addition to the inner and outer primers. The loop primers refer to 2 primers (one for each of strands composing a double-strand) comprising, at the 3' end, a nucleotide sequence complementary to a sequence in a loop formed by the annealing of complementary sequences present at the same strand of an amplification product obtained by the LAMP method. The use of the loop primers increases nucleic acid synthesis origins in number and achieves reduction in reaction time and enhancement in detection sensitivity (Pamphlet of International Publication No. WO 02/24902).

The oligonucleotide can be produced by a method known in the art and, for example, can be synthesized chemically. Alternatively, a natural nucleic acid is cleaved with a restriction enzyme or the like, and the resulting fragments may be modified or linked to compose a desired nucleotide sequence. Specifically, the oligonucleotide can be synthesized by use of an oligonucleotide synthesizer or the like. Alternatively, a production method known per se in the art can be used as a method for synthesis of an oligonucleotide comprising a nucleotide sequence with the substitution, deletion, insertion, or addition of one or several bases. For example, such an oligonucleotide may be synthesized by using site-specific mutagenesis, gene homologous recombination, primer extension, and PCR methods alone or in appropriate combination.

"Stringent hybridization conditions" used herein can be selected from those known generally. Examples of the stringent conditions include conditions involving overnight hybridization at 42° C. in a solution containing 50% formamide, 5×SSC (150 mM NaCl, 15 mM trisodium citrate), 50 mM sodium phosphate (pH 7.6), 5×Denhardt's solution, 10% dextran sulfate, and 20 µg/ml DNA, followed by primary washing at room temperature in 2×SSC/0.1% SDS and subsequent secondary washing at approximately 65° C. in 0.1× SSC/0.1% SDS.

Influenza viruses are RNA viruses. In the LAMP method using RNA as a template, a nucleic acid amplification reaction can be allowed to proceed in the same way as with template DNA by adding reverse transcriptase to a reaction solution for template DNA (RT-LAMP method).

The present inventors have conducted diligent studies on nucleotide sequences of primers of the LAMP method capable of quickly amplifying a nucleotide sequence specific to an H5 avian influenza virus and on combinations thereof and have consequently selected 4 primer sets A, B, C, and D described below from the nucleotide sequence of hemagglutinin of the H5 avian influenza virus (the nucleotide sequence represented by SEQ ID NO: 1). These primer sequences are totally different from primer sequences already reported (e.g., Patent Document 2) for NASBA (Nucleic Acid Sequence-Based Amplification) for H5 avian influenza virus detection.

```
(Primer set A)
FIP19c:
                                        (SEQ ID NO: 8)
5'-ACCATATTCCAACTCACTTTTCATAATTTCATTGCTCCAGAATATG
C-3'

BIP5:
                                        (SEQ ID NO: 9)
5'-CAAACTCCAATGGGGCATGGTGAGAGGGTGTAT-3'

F3m6:
                                        (SEQ ID NO: 4)
5'-GGAGTTCTTCTGGACAA-3'

B3m:
                                        (SEQ ID NO: 10)
5'-GTCGCAAGGACTAATCT-3'

LF24:
                                        (SEQ ID NO: 11)
5'-GAGTCCCCTTTCTTGACAAT-3'

LB1:
                                        (SEQ ID NO: 12)
5'-GATAAACTCTAGTATGCCA-3'

(Primer set B)
FIP:
                                        (SEQ ID NO: 19)
5'-GGGCATGTGTAACAGTAACGTTAAACAACTCGACAGAGCA-3'

BIP:
                                        (SEQ ID NO: 20)
5'-TGGAAAAGACACACAATGGGAACATCCAGCTACACTACAATC-3'

F3:
                                        (SEQ ID NO: 15)
5'-CAGATTTGCATTGGTTACCA-3'

B3:
                                        (SEQ ID NO: 21)
5'-CGTCACACATTGGGTTTC-3'
```

-continued

LF:
(SEQ ID NO: 22)
5'-TTCCATTATTGTGTCAACC-3'

LB8:
(SEQ ID NO: 23)
5'-CGATCTAGATGGAGTGAAGC-3'

(Primer set C)
FIP:
(SEQ ID NO: 30)
5'-CACATTGGGTTTCCGAGGAGATCTAGATGGAGTGAAGCC-3'

BIP:
(SEQ ID NO: 31)
5'-TTCATCAATGTGCCGGAATGGGTTGAAATCCCCTGGGTA-3'

F3:
(SEQ ID NO: 26)
5'-GGAAAAGACACACAATGGG-3'

B3:
(SEQ ID NO: 32)
5'-GCTCAATAGGTGTTTCAGTT-3'

LF6:
(SEQ ID NO: 33)
5'-CCAGCTACACTACAATCTCT-3'

LB6:
(SEQ ID NO: 34)
5'-TCCAGCCAATGACCTCTG-3'

(Primer set D)
FIP:
(SEQ ID NO: 41)
5'-TCGCAAGGACTAATCTGTTTGACATACACCCTCTCACCAT-3'

BIP:
(SEQ ID NO: 42)
5'-TACCCCTCAAAGAGAGAGAAGATCCTCCCTCTATAAAACCTG-3'

F3:
(SEQ ID NO: 37)
5'-TCTAGTATGCCATTCCACAA-3'

B3:
(SEQ ID NO: 43)
5'-ACCATCTACCATTCCCTG-3'

LF8:
(SEQ ID NO: 44)
5'-TCACATATTTGGGGCATTCC-3'

LB8:
(SEQ ID NO: 45)
5'-AGAGAGGACTATTTGGAGCT-3'

The present inventors have further conducted diligent studies on nucleotide sequences of primers of the LAMP method capable of quickly amplifying a nucleotide sequence specific to an H7 avian influenza virus and on combinations thereof and have consequently selected a primer set E described below from the nucleotide sequence of hemagglutinin of the H7 avian influenza virus (the nucleotide sequence represented by SEQ ID NO: 48).

(Primer set E)

22FIP:

(SEQ ID NO: 55)

5'-ACCACCCATCAATCAAACCTTCTATTTGGTGCTATAGCGG-3'

22BIP:

(SEQ ID NO: 56)

5'-TTCAGGCATCAAAATGCACAAGCCTGTTATTTGATCAATTGCTG-3'

-continued

22F3m:

(SEQ ID NO: 51)

5'-TTCCCGAAATCCCAAA-3'

22B3:

(SEQ ID NO: 57)

5'-GGTTAGTTTTTCTATAAGCCG-3'

22-9LF:

(SEQ ID NO: 58)

5'-CCCATCCATTTTCAATGAAAC-3'

22-9LB:

(SEQ ID NO: 59)

5'-ACTGCTGCAGATTACAAAAG-3'

An enzyme used in nucleic acid synthesis is not particularly limited as long as it is a template-dependent nucleic acid synthesis enzyme having strand displacement activities. Such an enzyme includes Bst DNA polymerase (large fragment), Bca (exo-) DNA polymerase, and the Klenow fragment of *E. coli* DNA polymerase I and preferably includes Bst DNA polymerase (large fragment).

Reverse transcriptase used in the RT-LAMP method is not particularly limited as long as it is an enzyme having activities of synthesizing cDNA with RNA as a template. Such an enzyme includes AMV, Cloned AMV, MMLV reverse transcriptases, Superscript II, ReverTra Ace, and Thermoscript and preferably includes AMV or Cloned AMV reverse transcriptase. Alternatively, the use of an enzyme having both reverse transcriptase and DNA polymerase activities, such as Bca DNA polymerase, can achieve an RT-LAMP reaction using a single enzyme.

The enzyme or reverse transcriptase used in nucleic acid synthesis may be purified from viruses, bacteria, or the like or may be prepared by a gene recombination technique. These enzymes may be modified by fragmentation, amino acid substitution, and so on.

A technique known in the art can be applied to the detection of nucleic acid amplification products after the LAMP reaction. For example, the nucleic acid amplification products can be detected by use of a labeled oligonucleotide specifically recognizing amplified nucleotide sequences or a fluorescent intercalator method (Japanese Patent Laid-Open No. 2001-242169), or can be detected easily by directly applying the reaction solution after the completion of reaction to agarose gel electrophoresis. In the agarose gel electrophoresis, the LAMP amplification products are detected in the form of a ladder of many bands differing in base length. Moreover, in the LAMP method, substrates are consumed in large amounts by nucleic acid synthesis, and pyrophosphoric acid ions as by-products are converted into magnesium pyrophosphate through its reaction with coexisting magnesium ions and makes the reaction solution cloudy to the extent that can be observed visually. Thus, the nucleic acid amplification reaction may be detected by confirming this cloudiness by use of a measurement apparatus that can optically observe time-dependent rises in turbidity after the completion of reaction or during reaction, for example, by confirming changes in absorbance at 400 nm by use of a usual spectrophotometer (Pamphlet of International Publication No. WO 01/83817).

A variety of reagents necessary for the detection of nucleic acid amplification by use of the primers of the present invention can be packaged in advance into a kit. Specifically, a kit provided comprises a variety of oligonucleotides necessary as the primers of the present invention or the loop primers, 4 dNTPs serving as substrates for nucleic acid synthesis, DNA polymerase for performing nucleic acid synthesis, an enzyme having reverse transcription activities, buffer solutions or salts that provide conditions suitable to an enzyme reaction, protective agents for stabilizing the enzymes or the templates and optionally comprises reagents necessary for the detection of reaction products.

EXAMPLES

Hereinafter, the present invention will be described specifically with reference to Examples. However, the present invention is not limited to them by any means.

Example 1

Confirmation of Reactivity of Primer Sets for H5 Avian Influenza Virus

Primer reactivity was confirmed by a method described below. The composition of a reaction solution for nucleic acid amplification by a LAMP method is as described below. Primer synthesis was requested to QIAGEN, and the primers were used after OPC (reverse phase column cartridge) purification.
20 mM Tris-HCl pH 8.8
10 mM KCl
8 mM $MgSO_4$
1.4 mM dNTPs
10 mM $(NH_4)_2SO_4$
0.8 M Betaine (SIGMA)
0.1% Tween 20
1.6 µM FIP
1.6 µM BIP
0.2 µM F3
0.2 µM B3
0.8 µM LF
0.8 µM LB
AMV Reverse Transcriptase 2 U (Finnzyme)
Bst DNA polymerase 16 U (NEB)

The reaction solution was supplemented with $10^4$ copies of H5 plasmid DNA (HK/213/03, provided by the National Institute of Infectious Diseases) to perform an RT-LAMP reaction at 62.5° C. for 60 minutes. The reaction was detected in real time by use of a real-time turbidity measurement apparatus LA-320C (Eiken Chemical Co., Ltd.). As a result, amplification was confirmed in 4 primer sets (primer sets A, B, C, and D).

These 4 sets were further subjected to a specificity test using, as templates, RNAs extracted from cultured viruses New Caledonia (H1N1) and Panama (H3N2). FIG. 1 is a graph showing a result of the specificity test. As shown in FIG. 1, the amplification of the H1 and H3 subtypes was not confirmed when any of the primer sets were used. These results revealed that all the primer sets are highly specific to the H5 subtype.

Figure 2:
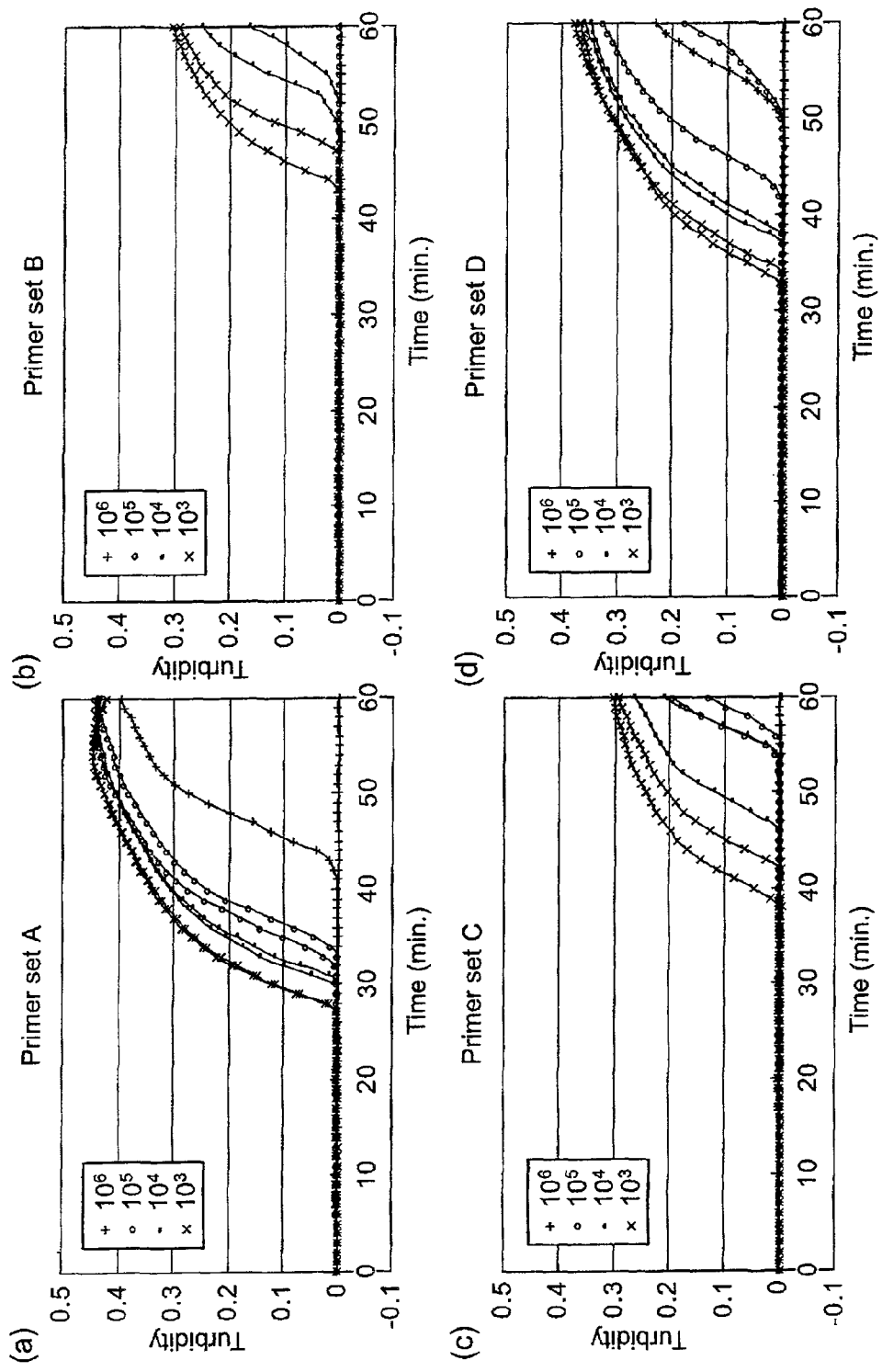
FIG. 2 is a graph showing a result of a sensitivity test of the primer sets for an H5 avian influenza virus.

Next, a sensitivity test was conducted by use of RNA extracted from a cultured virus Vietnam/JP1203/04 (H5N1). Because the amount of a template was unknown for the extracted RNA, the extracted RNA was diluted $10^3$ to $10^6$ folds with RNase-free sterilized water and used as a template sample. FIG. 2 is a graph showing a result of the sensitivity test. Amplification was confirmed even in the sample diluted $10^5$ folds when the primer set A was used, revealing that the primer set A is most highly sensitive.

Example 2

Confirmation of Products Amplified with Primer Set for H5 Avian Influenza Virus

Figure 3:
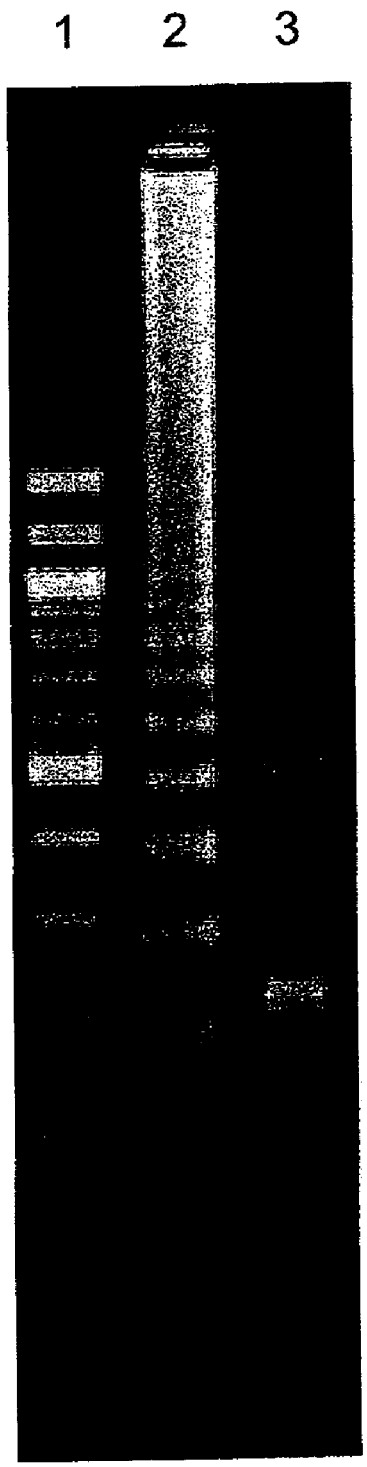
FIG. 3 is a diagram showing a result of electrophoresis of products amplified with the primer set for an H5 avian influenza virus. Lane 1 represents a 100 bp ladder marker, Lane 2 represents a LAMP product sample, and Lane 3 represents a LAMP product sample treated with DdeI.

LAMP products amplified with the primer set A were confirmed by use of electrophoresis and a restriction enzyme DdeI. FIG. 3 is a diagram showing a result of the electrophoresis. As seen from the Lane 2 of FIG. 3, a ladder pattern specific to the LAMP product was confirmed. Moreover, digestion was confirmed in the sample treated with DdeI (Lane 3). These results revealed that the target sequence is specifically amplified.

Example 3

Evaluation of Primer Set for H5 Avian Influenza Virus (Cross Matching Test)

Eighteen samples in total were used which included human influenza viruses A/New Caledonia/20/99 (H1N1), A/Panama/2007/99 (H3N2), B/Shangdong/07/97, and B/Shanghai/361/2002, and avian influenza viruses H1 to H15 (except for H5). RNA was extracted from each of the cultured viruses by use of QIAamp Viral RNA Kit (QIAGEN), and 5 µL extracts were used in an RT-LAMP reaction (the primer set A was used as primers).

Figure 4:
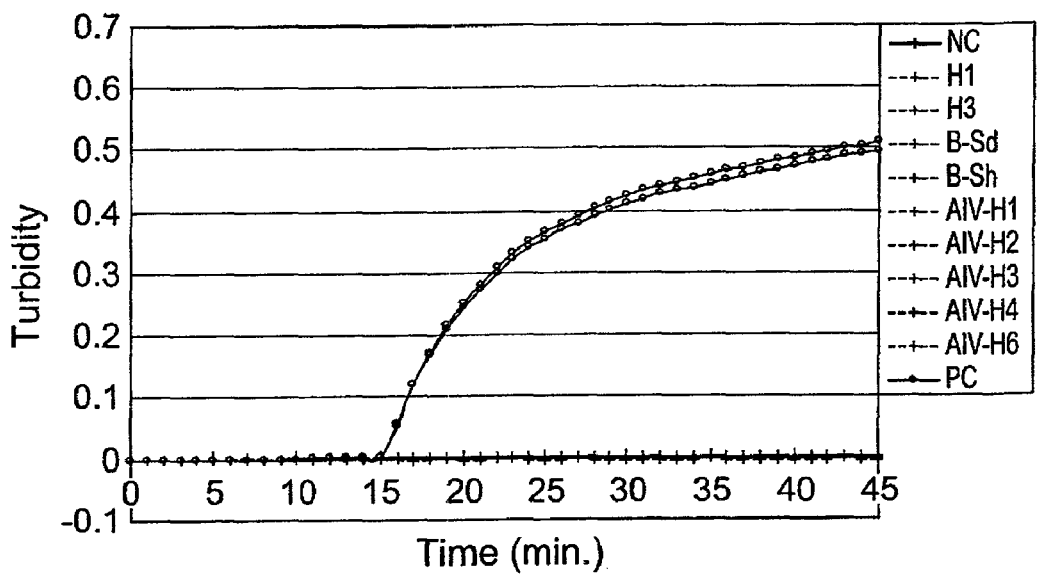
Figure 4:
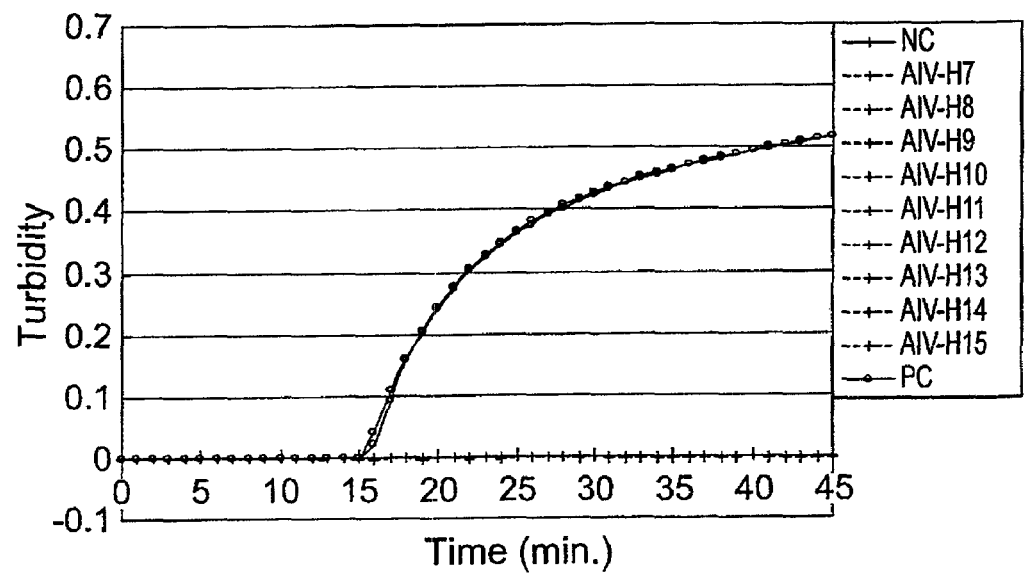
Figure 5:
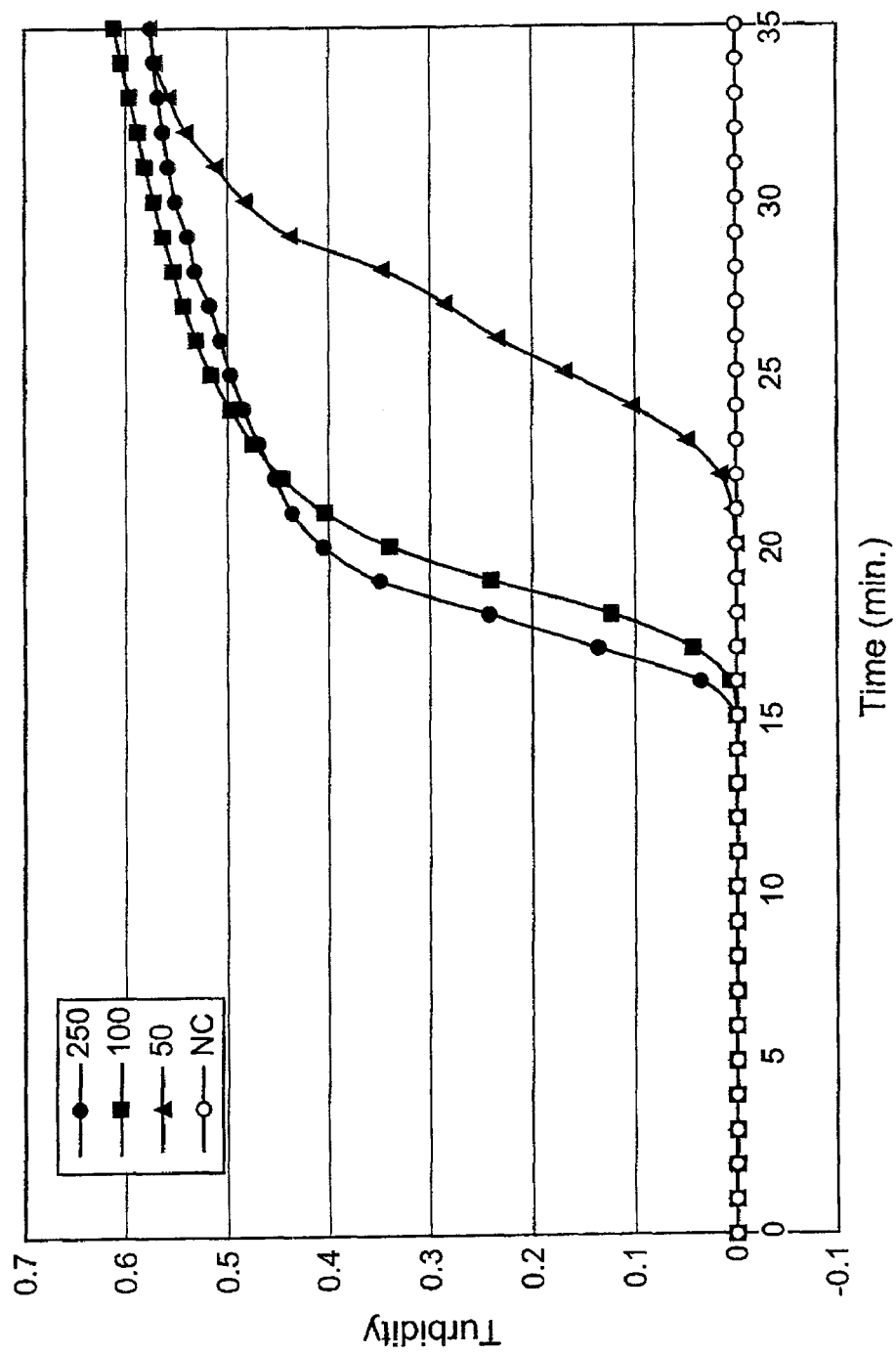
FIG. 5 is a graph showing a result of a reactivity confirmation test of a primer set for an H7 avian influenza virus. 250, 100, and 50 represent the amounts of RNA added (copy/assay), and NC represents a negative control.
Figure 6:
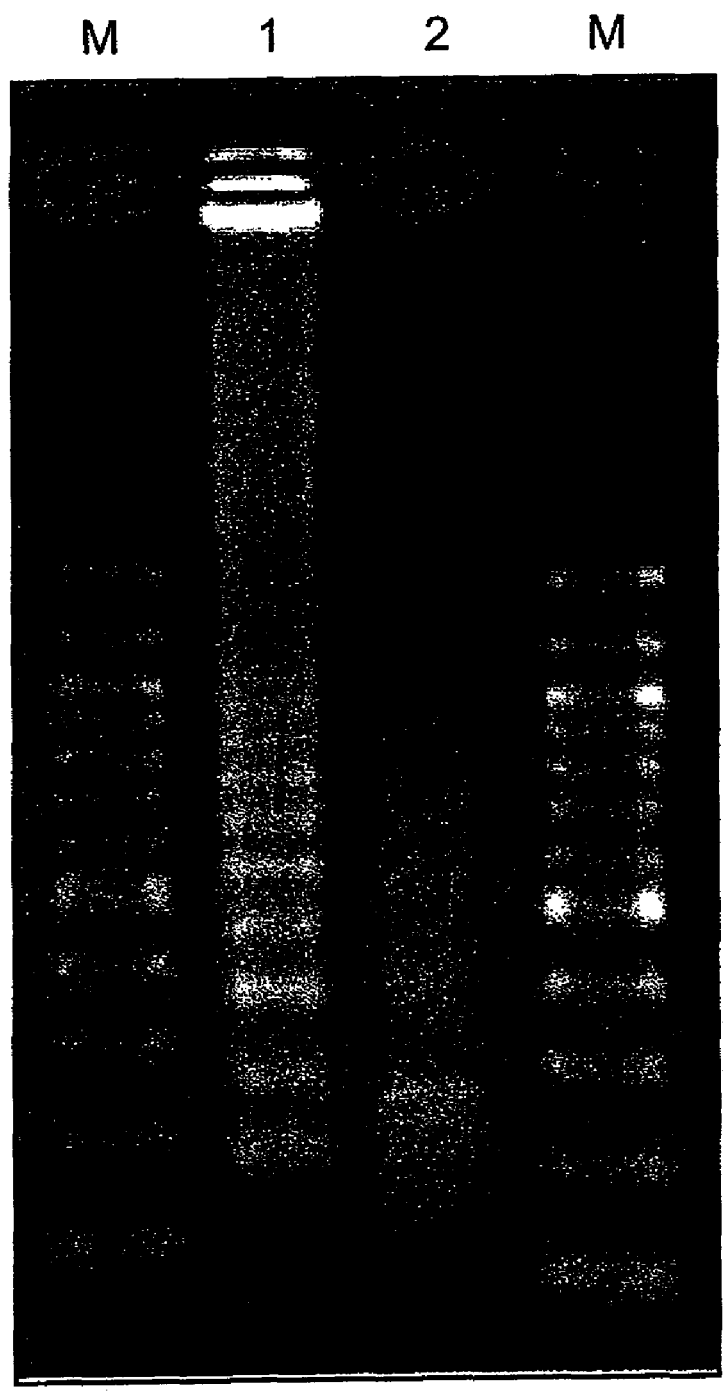
FIG. 6 is a diagram showing a result of electrophoresis of products amplified with the primer set for an H7 avian influenza virus. Lane M represents a 100 bp ladder marker, Lane 1 represents a LAMP product sample, and Lane 2 represents a LAMP product sample treated with PstI.
Figure 7:
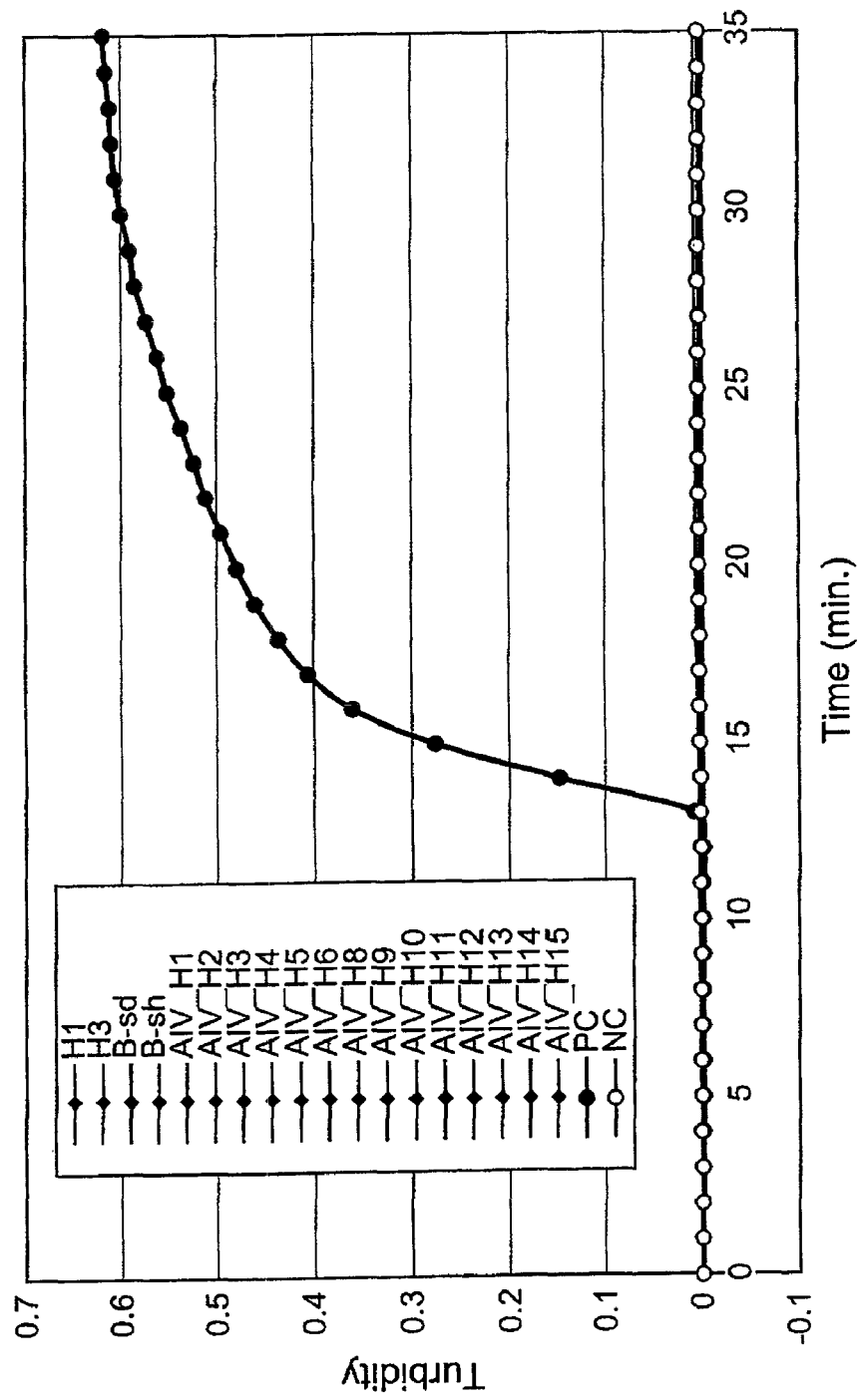
FIG. 7 is a graph showing a result of a cross matching test of the primer set for an H7 avian influenza virus. H1 and H3 represent human influenza viruses H1 and H3, respectively, and B-sd represents B/Shandong/07/97, B-sh represents B/Shanghai/361/2002, AIV-H1 and so on represents avian influenza virus H1 and so on, PC represents a positive control, and NC represents a negative control.
Figure 8:
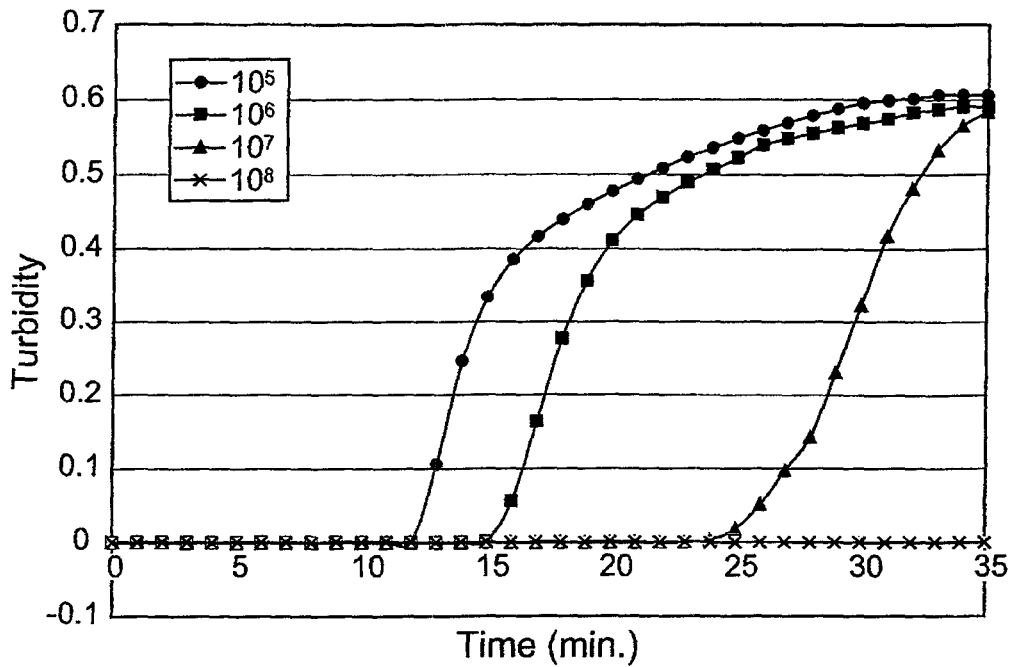
FIG. 8 is a graph showing a result of the reactivity of the primer set for an H7 avian influenza virus to various strains.
Figure 8:
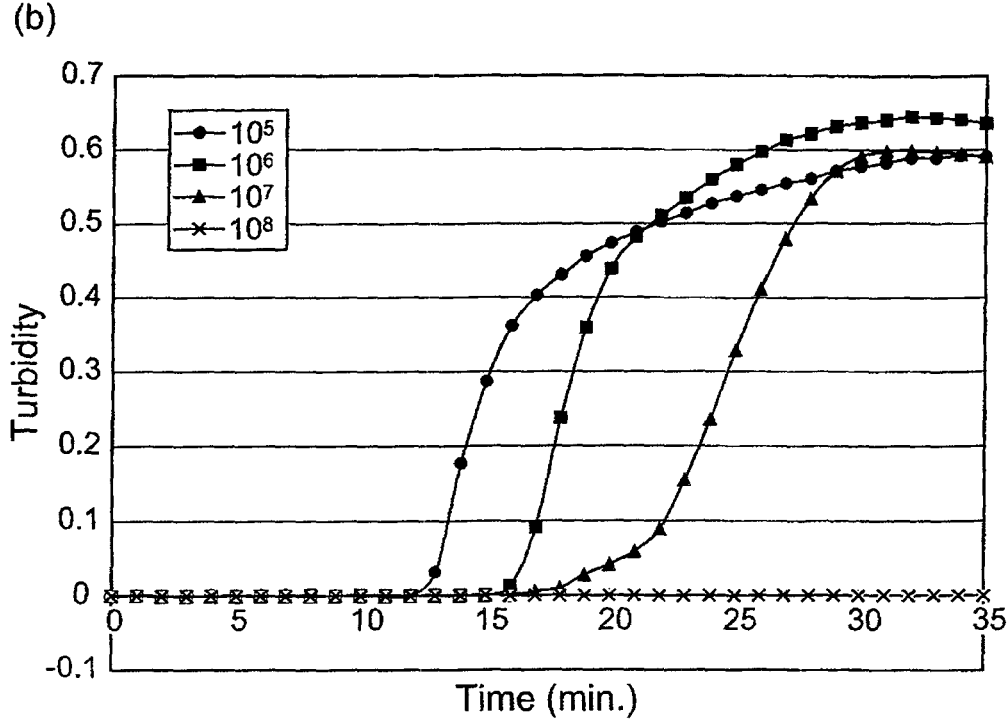
Figure 9:
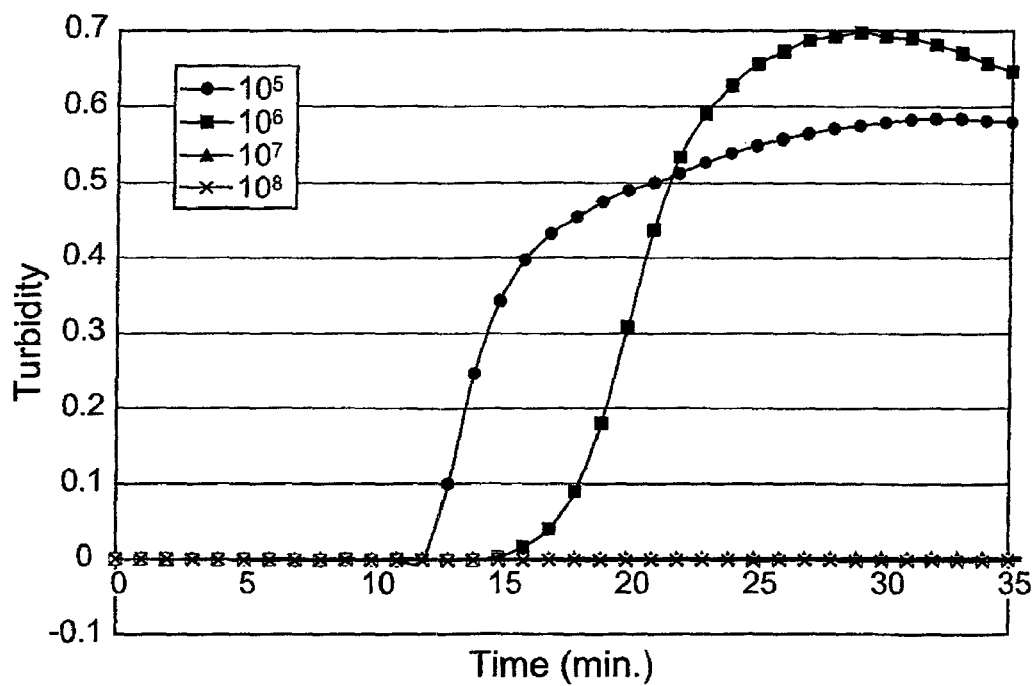
FIG. 9 is a graph showing a result of the reactivity of the primer set for an H7 avian influenza virus to various strains.
Figure 9:
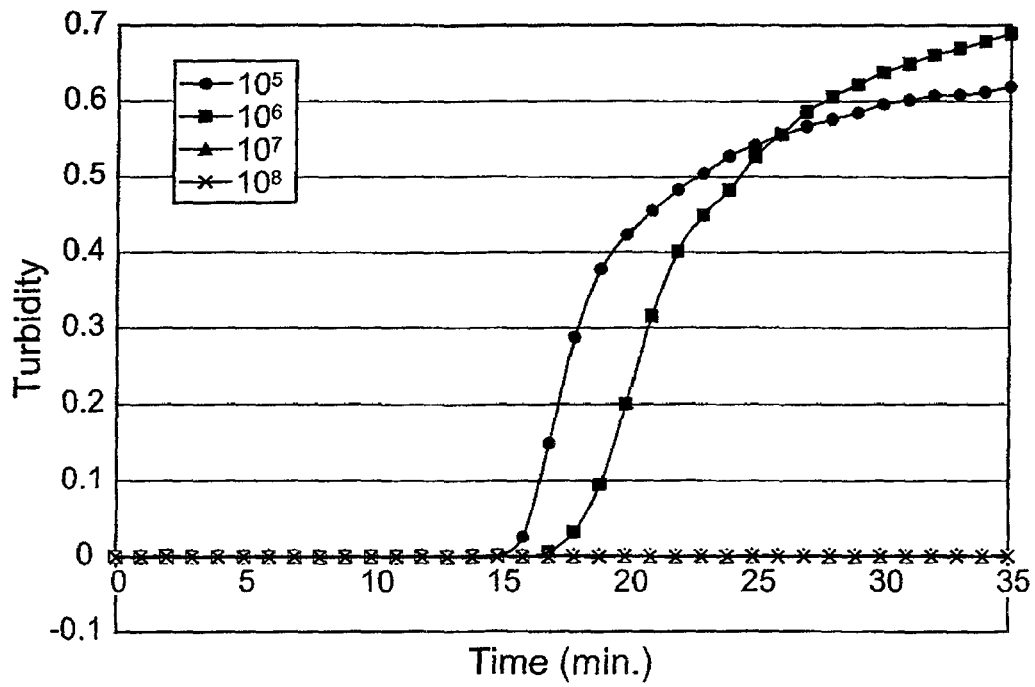

As seen from FIGS. 4(a) and 4(b), amplification was not observed in the RT-LAMP method using any of the samples. These results revealed that the RT-LAMP method is highly specific.

Example 4

Evaluation of Primer Set for H5 Avian Influenza Virus (Sensitivity Test)

An avian influenza H5 strain (CH/Yamaguchi 7/04) whose infection was confirmed in Yamaguchi Prefecture, Japan in 2004 and an avian influenza H5 strain (VN/JP1203/04) whose infection was confirmed in Vietnam in 2004 were used as template samples. RNA extracted from each of the cultured viruses was serially diluted ($10^4$ to $10^8$) with RNase-free sterilized water, and 10 µL diluents and 5 µL diluents were used in an RT-PCR method and an RT-LAMP method (the primer set A was used as primers), respectively.

The RT-PCR method was performed by modifying conditions published by the website of the Infectious Disease Surveillance Center of the National Institute of Infectious Diseases. Specifically, a commercially available kit (TaKaRa One Step RNA PCR Kit (AMV)) was used to perform a reverse transcription reaction at 50° C. for 30 minutes, treatment at 94° C. for 2 minutes, 30 cycles of 94° C. for 1 minute, 45° C. for 1 minute, and 72° C. for 1 minute, and an elongation reaction at 72° C. for 10 minutes, followed by storage at 4° C.

Primers and the composition of a reaction solution used in the RT-PCR method are as described below.

```
Primers (length of PCR product: 708 bp)
H5 515f:
                                        (SEQ ID NO: 46)
5'-CATACCCAACAATAAAGAGG-3'

H5 1220r:
                                        (SEQ ID NO: 47)
5'-GTGTTCATTTTGTTAATGAT-3'
```

Reaction Solution
10 µL of RNA extract
5 µL of 10×One Step RNA PCR Buffer
5 µL of 10 mM dNTPs
10 µL of 25 mM $MgCl_2$
1 µL of RNase Inhibitor
1 µL of AMV RTase 1 μL of AMV-Optimized Taq
2 μL of H5 515f (10 μM)
2 μL of H5 1220r (10 μM)
The reaction solution was adjusted to 50 μL by the appropriate addition of RNase-free sterilized water.

Results of amplification by the RT-PCR and RT-LAMP methods are summarized in Table 1. In Table 1, the boxes of the RT-LAMP method show the rate of a sample confirmed to be amplified. The amplification by RT-PCR was confirmed by visually observing the result of electrophoresis (in Table 1, + means that the amplification could be detected, and − means the amplification could not be detected).

TABLE 1

| Sample | Measurement method | Dilution rate | | | | |
|---|---|---|---|---|---|---|
| | | $10^4$ | $10^5$ | $10^6$ | $10^7$ | $10^8$ |
| CH/Yamaguchi 7/04 | RT-LAMP | 2/2 | 2/2 | 2/2 | 2/2 | 0/2 |
| | RT-PCR | + | + | − | − | − |
| VN/JP1203/04 | RT-LAMP | 2/2 | 2/2 | 2/2 | 2/2 | 1/2 |
| | RT-PCR | + | + | + | − | − |

When the RT-LAMP and RT-PCR methods were compared, the RT-LAMP method had sensitivity 10 to 100 times higher to any of the strains.

Example 5

Confirmation of Reactivity of Primer Set for H7 Avian Influenza Virus

The reactivity of a primer set E was confirmed by a method described below. The composition of a reaction solution for nucleic acid amplification by a LAMP method is as described below. Primer synthesis was requested to QIAGEN, and the primers were used after OPC (reverse phase column cartridge) purification.

20 mM Tris-HCl pH 8.8

10 mM KCl 8 mM $MgSO_4$ 1.4 mM dNTPs 10 mM $(NH_4)_2SO_4$ 0.8 M Betaine (SIGMA)

0.1% Tween 20

1.6 μM FIP 1.6 μM BIP 0.2 μM F3

0.2 μM B3

0.8 μM LF 0.8 μM LB

AMV Reverse Transcriptase 2 U (Finnzyme)

Bst DNA polymerase 16 U (NEB)

The nucleotide sequence of A/Netherlands/219/2003 (H7N7) (strain separated from a death case in Netherlands) (a fragment comprising the nucleotide sequence represented by SEQ ID NO: 48) was incorporated into a cloning vector to prepare RNA through a transcription reaction. The prepared RNA was added at 250, 100, or 50 copies/assay to the reaction solution, and an amplification reaction and detection at 62.5° C. for 35 minutes were performed by use of a real-time turbidity measurement apparatus LA-200 (Teramecs Co., Ltd.).

FIG. 5 shows a result of real-time detection of 250, 100, and 50 copies/assay of RNA added and a negative control. This result demonstrated that up to 50 copies/assay are detected.

Example 6

Confirmation of Products Amplified with Primer Set for H7 Avian Influenza Virus LAMP products amplified with the primer set E were confirmed by use of electrophoresis and a restriction enzyme PstI. FIG. 6 is a graph showing a result of the electrophoresis. M represents a 100 bp ladder marker, Lane 1 represents an untreated LAMP product sample, and Lane 2 represents a LAMP product sample treated with PstI. As seen from the Lane 1 of FIG. 6, a ladder pattern specific to the LAMP product was confirmed. Moreover, digestion was confirmed in the sample treated with PstI (Lane 2). These results revealed that the target sequence is specifically amplified.

Example 7

Evaluation of Primer Set for H7 Avian Influenza Virus (Cross Matching Test)

To examine primer specificity, eighteen samples in total were used which included human influenza viruses A/New Caledonia/20/99 (H1N1), A/Panama/2007/99 (H3N2), B/Shangdong/07/97, and B/Shanghai/361/2002, and avian influenza viruses H1 to H15 (except for H7). RNA was extracted from each of the cultured viruses by use of QIAamp Viral RNA Kit (QIAGEN), and the extracted RNA was diluted 100 folds and used in an RT-LAMP reaction. The RNA prepared in Example 5 was used as a positive control (PC), and distilled water was used as a negative control.

As seen from FIG. 7, amplification was not observed in any of the samples. These results revealed that the primer set of the present invention is highly specific.

Example 8

Evaluation of Primer Set for H7 Avian Influenza Virus (Reactivity to Various Strains)

Four H7 avian influenza virus genomes were used as template samples to examine sensitivity to each virus. RNA extracted from each of the cultured viruses was serially diluted ($10^5$ to $10^8$) with RNase-free sterilized water, and the 5 μL diluents were used.

FIGS. 8 and 9 show a result of the real-time detection using each virus genome as a template sample. Up to $10^7$ diluents could be detected for A/Netherlands/219/2003 (H7N7) and A/Netherlands/33/00 (H7N7) (see FIG. 8), while up to $10^6$ diluents could be detected for A/mallard/Netherlands/12/2003 (H7N3) and A/wigeon/Osaka/1/2001 (H7N7) (see FIG. 9). These results demonstrated that the primer set of the present invention reacts with these 4 strains.

INDUSTRIAL APPLICABILITY

According to the present invention, an H5 or H7 avian influenza virus can be detected quickly with high sensitivity.

The invention claimed is:
1. An oligonucleotide primer set consisting of
(i) an inner primer set comprising a primer consisting of the nucleotide sequence of SEQ ID NO:55 and a primer consisting of SEQ ID NO: 56; and
(ii) an outer primer set comprising the nucleotide sequence of SEQ ID NOs: 51 and 57,
wherein the oligonucleotide primer set is suitable for amplification of a nucleic acid with a loop-mediated isothermal amplification method.
2. An oligonucleotide primer set consisting of
(i) an inner primer set comprising a primer consisting of the nucleotide sequence of SEQ ID NO:55 and a primer consisting of SEQ ID NO: 56;
(ii) an outer primer set comprising the nucleotide sequence of SEQ ID NOs: 51 and 57; and
(iii) a loop primer set comprising the nucleotide sequence of SEQ ID NOs: 58 and 59,
wherein the oligonucleotide primer set is suitable for amplification of a nucleic acid with a loop-mediated isothermal amplification method.
3. A method for detection of an H7 avian influenza virus comprising performing an amplification reaction of a target nucleic acid region of an H7 avian influenza virus, wherein the amplification reaction is a LAMP method, with the oligonucleotide primer set according to claim 1 or 2.
4. A method for influenza diagnosis comprising detecting amplification of a target nucleic acid region of an H7 avian influenza virus with the oligonucleotide primer set according to claim 1 or 2 and thereby diagnosing the presence or absence of infection with the H7 avian influenza virus.
5. A kit for influenza diagnosis comprising the oligonucleotide primer set according to claim 1 or 2.

* * * * *

SEQUENCE LISTING

<160> NUMBER OF SEQ ID NOS: 59

<210> SEQ ID NO 1
<211> LENGTH: 1674
<212> TYPE: DNA
<213> ORGANISM: Avian influenza virus

<400> SEQUENCE: 1

```
agtcttgtta aaagtgatca gatttgcatt ggttaccatg caaacaactc gacagagcag      60
gttgacacaa taatggaaaa gaacgttact gttacacatg cccaagacat attggaaaag     120
acacacaatg ggaagctctg cgatctagat ggagtgaagc ctctaatttt gagagattgt     180
agtgtagctg gatggctcct cggaaaccca atgtgtgacg aattcatcaa tgtgccggaa     240
tggtcttaca tagtggagaa ggccagtcca gccaatgacc tctgttaccc aggggatttc     300
aacgactatg aagaactgaa acacctattg agcagaataa accattttga gaaaattcag     360
atcatcccca aaagttcttg gtccaatcat gaagcctcat caggggtgag ctcagcatgt     420
ccatatcttg ggaagtcctc cttttttcaga aatgtggtat ggcttatcaa aagaacagt     480
acatacccaa caataaagag gagctataat aataccaacc aagaagatct tttggtactg     540
tgggggattc accatcctaa tgatgcggca gagcagacaa agctctatca aaacccaacc     600
acctatattt ccgttggaac atcaacacta aaccagagat tggtaccaaa aatagctact     660
agatccaaag taaacgggca aagtggaaga atggagttct tctggacaat tttaaagccg     720
aatgatgcta tcaatttcga gagtaatgga aatttcattg ctccagaata tgcatacaaa     780
attgtcaaga aaggggactc agcaattatg aaaagtgaat tggaatatgg taactgcaac     840
accaagtgtc aaactccaat gggggcgata aactctagta tgccattcca caacatacac     900
cctctcacca tcggggaatg ccccaaatat gtgaaatcaa acagattagt ccttgcgact     960
ggactcagaa ataccctca aagagagaga agaagaaaaa agagaggact atttggagct    1020
atagcaggtt ttatagaggg aggatggcag ggaatggtag atggttggta tgggtaccac    1080
catagcaatg agcaggggag tggatacgct gcagacaaag aatccactca aaaggcaata    1140
gatggagtta ccaataaggt caactcgatc attgacaaaa tgaacactca gtttgaggcc    1200
gttggaaggg aatttaataa cttagaaagg agaatagaaa atttaaacaa gaagatggaa    1260
gacggattcc tagatgtctg gacttataat gctgaacttc tggttctcat ggaaaatgag    1320
agaactctag actttcacga ctcaaatgtc aagaaccttt acgacaaggt ccgactacag    1380
cttagggata tgcaaagga gctgggtaac ggctgtttcg agttctatca caaatgtgat    1440
aatgaatgta tggaaagtgt aaaaaacgga acgtatgact acccgcagta ttcagaagaa    1500
gcaagactaa acagagagga aataagtgga gtaaaattgg aatcaatggg aacttaccaa    1560
atactgtcaa tttattcaac agtggcgagt tccctagcac tggcaatcat ggtagctggt    1620
ctatctttat ggatgtgctc caatggatcg ttacaatgca gaatttgcat ttaa           1674
```

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
aattatgaaa agtgagttgg aatatggt                                           28
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcattgctcc agaatatgc                                              19

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggagttcttc tggacaa                                                17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caaactccaa tgggggc                                                17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atacaccctc tcaccat                                                17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agattagtcc ttgcgac                                                17

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accatattcc aactcacttt tcataatttc attgctccag aatatgc                47

```
<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caaactccaa tgggggcatg gtgagagggt gtat                                 34

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcgcaagga ctaatct                                                    17

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagtcccctt tcttgacaat                                                 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gataaactct agtatgcca                                                  19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aacgttactg ttacacatgc cc                                              22

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaacaactcg acagagca                                                   18

<210> SEQ ID NO 15
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagatttgca ttggttacca                                               20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggaaaagac acacaatggg aa                                            22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gattgtagtg tagctggatg                                               20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaaacccaat gtgtgacg                                                 18

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggcatgtgt aacagtaacg ttaaacaact cgacagagca                         40

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggaaaagac acacaatggg aacatccagc tacactacaa tc                      42

<210> SEQ ID NO 21
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 21
cgtcacacat tgggtttc                                                   18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttccattatt gtgtcaacc                                                  19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgatctagat ggagtgaagc                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctcctcggaa acccaatgtg                                                 20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atctagatgg agtgaagcc                                                  19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggaaaagaca cacaatggg                                                  19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

```
                                                primer

<400> SEQUENCE: 27
ttcatcaatg tgccggaatg g                                                 21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tacccagggg atttcaac                                                     18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aactgaaaca cctattgagc                                                   20

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacattgggt ttccgaggag atctagatgg agtgaagcc                              39

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcatcaatg tgccggaatg ggttgaaatc ccctgggta                              39

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctcaatagg tgtttcagtt                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 33
ccagctacac tacaatctct                                             20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tccagccaat gacctctg                                               18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcaaacagat tagtccttgc ga                                          22

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
catacaccct ctcaccat                                               18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tctagtatgc cattccacaa                                             20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tacccctcaa agagagagaa ga                                          22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
```
caggttttat agagggagga 20

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 40
cagggaatgg tagatggt 18

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 41
tcgcaaggac taatctgttt gacatacacc ctctcaccat 40

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 42
tacccctcaa agagagagaa gatcctccct ctataaaacc tg 42

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 43
accatctacc attccctg 18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 44
tcacatattt ggggcattcc 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 45
agagaggact atttggagct 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
catacccaac aataaagagg                                             20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtgttcattt tgttaatgat                                             20

<210> SEQ ID NO 48
<211> LENGTH: 1737
<212> TYPE: DNA
<213> ORGANISM: Avian influenza virus

<400> SEQUENCE: 48
agcaaaagca ggggatacaa aatgaacact caaatcctgg tattcgctct ggtggcgagc     60
attccgacaa atgcagacaa gatctgcctt gggcatcatg ccgtgtcaaa cgggactaaa   120
gtaaacacat taactgagag aggagtggaa gtcgttaatg caactgaaac ggtgaacga    180
acaaacgttc ccaggatctg ctcaaaaggg aaaaggacag ttgacctcgg tcaatgtgga   240
cttctgggaa caatcactgg gccaccccaa tgtgaccaat cctagaatt ttcggccgac    300
ttaattattg agaggcgaga aggaagtgat gtctgttatc ctgggaaatt cgtgaatgaa   360
gaagctctga ggcaaattct cagagagtca ggcggaattg acaaggagac aatgggattc   420
acctacagcg gaataagaac taatggaaca accagtgcat gtaggagatc aggatcttca   480
ttctatgcag agatgaaatg gctcctgtca aacacagaca atgctgcttt cccgcaaatg   540
actaagtcat acaagaacac aaggaaagac ccagctctga taatatgggg gatccaccat   600
tccggatcaa ctacagaaca gaccaagcta tatgggagtg aaacaaact gataacagtt    660
gggagttcta attaccaaca gtcctttgta ccgagtccag gagcgagacc acaagtgaat   720
ggccaatctg gaagaattga ctttcattgg ctgatactaa accctaatga cacggtcact   780
ttcagtttca tggggccttc atagctcca gaccgtgcaa gctttctgag agggaagtcc    840
atgggaattc agagtgaagt acaggttgat gccaattgtg aaggagattg ctatcatagt   900
ggagggacaa taataagtaa tttgcccttt cagaacataa atagcagggc agtaggaaaa   960
tgtccgagat atgttaagca agagagtctg ctgttggcaa caggaatgaa gaatgttccc  1020
gaaatcccaa agaggaggag gagaggccta tttggtgcta tagcgggttt cattgaaaat  1080
ggatgggaag gtttgattga tgggtggtat ggcttcaggc atcaaaatgc acaaggggag  1140
ggaactgctg cagattacaa aagcacccaa tcagcaattg atcaaataac agggaaatta  1200
aatcggctta tagaaaaaac taaccaacag tttgagttaa tagacaacga attcactgag  1260
gttgaaaggc aaattggcaa tgtgataaac tggaccagag attccatgac agaagtgtgg  1320
tcctataacg ctgaactctt agtagcaatg gagaatcagc acacaattga tctggccgac  1380

```
tcagaaatga acaaactgta cgaacgagtg aagagacaac tgagagagaa tgccgaagaa    1440
gatggcactg gttgcttcga aatatttcac aagtgtgatg acgactgcat ggccagtatt    1500
agaaacaaca cctatgatca cagcaagtac agggaagaag caatacaaaa tagaatacag    1560
attgacccag tcaaactaag cagcggctac aaagatgtga tactttggtt tagcttcggg    1620
gcatcatgtt tcatacttct ggccattgca atgggccttg tcttcatatg tgtgaagaat    1680
ggaaacatgc ggtgcactat ttgtatataa gtttggaaaa acaccttgt ttctact       1737
```

```
<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaggtttgat tgatgggtgg t                                              21

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctatttggtg ctatagcgg                                                 19

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttcccgaaat cccaaa                                                    16

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttcaggcatc aaaatgcaca ag                                             22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cagcaattga tcaaataaca gg                                             22

<210> SEQ ID NO 54
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cggcttatag aaaaaactaa cc                                              22

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
accacccatc aatcaaacct tctatttggt gctatagcgg                           40

<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttcaggcatc aaaatgcaca agcctgttat ttgatcaatt gctg                      44

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggttagtttt ttctataagc cg                                              22

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cccatccatt ttcaatgaaa c                                               21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
actgctgcag attacaaaag                                                 20
```